(12) United States Patent
Paul et al.

(10) Patent No.: US 10,961,212 B2
(45) Date of Patent: Mar. 30, 2021

(54) FUROIC ACID PREPARATION METHOD

(71) Applicants: Université de Lille, Lille (FR); Ecole Centrale de Lille, Villeneuve d'Ascq (FR); Centre national de la recherche scientifique, Paris (FR); Alma Mater Studiorum—Universitá di Bologna, Bologna (IT)

(72) Inventors: Sébastien Paul, Thun Saint Amand (FR); Francesco Santarelli, Senigallia (IT); Robert Wojcieszak, Lille (FR); Franck Dumeignil, Fretin (FR); Fabrizio Cavani, Modena (IT)

(73) Assignees: UNIVERSITÉ DE LILLE, Lille (FR); ECOLE CENTRALE DE LILLE, Villeneuve d'Ascq (FR); CENTRE NATIONAL DE LA RECHERCHE SCIENTIFIQUE, Paris (FR); ALMA MATER STUDIORUM—UNIVERSITA' DI BOLOGNA, Bologna (IT)

( * ) Notice: Subject to any disclaimer, the term of this patent is extended or adjusted under 35 U.S.C. 154(b) by 10 days.

(21) Appl. No.: 16/085,530

(22) PCT Filed: Mar. 16, 2017

(86) PCT No.: PCT/EP2017/056264
§ 371 (c)(1),
(2) Date: Sep. 14, 2018

(87) PCT Pub. No.: WO2017/158106
PCT Pub. Date: Sep. 21, 2017

(65) Prior Publication Data
US 2019/0382361 A1 Dec. 19, 2019

(30) Foreign Application Priority Data

Mar. 16, 2016 (FR) ...................... 1652217

(51) Int. Cl.
| | |
|---|---|
| C07D 307/46 | (2006.01) |
| C07D 307/68 | (2006.01) |
| B01J 21/02 | (2006.01) |
| B01J 21/06 | (2006.01) |
| B01J 23/52 | (2006.01) |
| B01J 35/00 | (2006.01) |
| B01J 35/10 | (2006.01) |

(52) U.S. Cl.
CPC ............ C07D 307/68 (2013.01); B01J 21/02 (2013.01); B01J 21/066 (2013.01); B01J 23/52 (2013.01); B01J 35/006 (2013.01); B01J 35/0013 (2013.01); B01J 35/0066 (2013.01); B01J 35/1009 (2013.01); B01J 35/1014 (2013.01)

(58) Field of Classification Search
CPC ........................... C07D 307/46; C07D 307/48
USPC .................................................. 549/484, 485
See application file for complete search history.

(56) References Cited

FOREIGN PATENT DOCUMENTS

WO    WO 2013/096998 A1    7/2013

OTHER PUBLICATIONS

Gupta, N.K., et al., Hydrotalcite-supported gold-nanoparticle-catalyzed highly efficient base-free aqueous oxidation of 5-hydroxymethylfurfural into 2,5-furandicarboxylic acid under atmospheric oxygen pressure, Green Chemistry, vol. 13, No. 4, pp. 824-827, 2011.
International Search Report, dated May 12, 2017, in International Application No. PCT/EP2017/056264.
Zhang, Z., et al., Recent Advances in the Catalytic Synthesis of 2,5-Furandicarboxylic Acid and Its Derivatives, ACS Catalysis, vol. 5, No. 11, pp. 6259-6544, 2015.

*Primary Examiner* — Charanjit Aulakh
(74) *Attorney, Agent, or Firm* — Knobbe, Martens, Olson & Bear LLP

(57) ABSTRACT

A method is for the preparation of furoic acid or of one of its derivatives of formula (I):

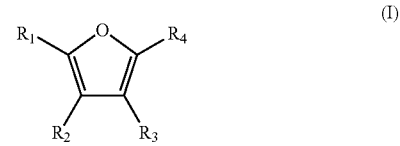

in which $R_1$, $R_2$, $R_3$ and $R_4$ represent, independently of each other, a hydrogen atom, a linear or branched $C_1$-$C_6$ alkyl group, a —C(=O)—H group or a —COOH group, by heterogeneous catalytic oxidation of furfural or a derivative thereof of formula (II). The oxidation is carried out in the presence of a supported catalyst based on gold nanoparticles, and in a non-alkaline aqueous medium. A composition useful in the method includes at least furfural and supported gold nanoparticles.

18 Claims, No Drawings

FUROIC ACID PREPARATION METHOD

PRIORITY AND CROSS REFERENCE TO RELATED APPLICATIONS

This application is the U.S. National Phase Application under 35 U.S.C. § 371 of International Application No. PCT/EP2017/056264, filed Mar. 16, 2017, designating the U.S. and published as WO 2017/158106 A1 on Sep. 21, 2017, which claims the benefit of French Application No. FR 1652217, filed Mar. 16, 2016. Any and all applications for which a foreign or a domestic priority is claimed is/are identified in the Application Data Sheet filed herewith and is/are hereby incorporated by reference in their entireties under 37 C.F.R. § 1.57.

FIELD

The present invention relates to furoic acid preparation methods.

SUMMARY

The present invention relates to a heterogeneous catalytic method for the preparation of furoic acid or a derivative thereof from furfural or one of its derivatives in the liquid phase.

DETAILED DESCRIPTION

The present invention relates to a heterogeneous catalytic method for the preparation of furoic acid or a derivative thereof from furfural or one of its derivatives in the liquid phase.

Furoic acid (also known as 2-furoic acid, or furan-2-carboxylic acid, or alpha-furoic acid) is an important compound for industry and may be used in various fields of application.

In particular, furoic acid may be used as a preservative in pasteurization and sterilization steps in the field of food, thus acting as a bactericidal and fungicidal agent. It may also be used as a flavoring agent.

This compound may be useful in the preparation of nylons in the field of biomedical research.

Furoic acid also provides furoic acid esters and is frequently used as an intermediate in the chemical, pharmaceutical and agrochemical industries.

Finally, it may eventually play an important role in the field of optical technologies because the polar organic crystals that it forms in the solid state could be key elements of future photonic technologies allowing the storage of images and information (Uma et al., Optik—International Journal for Light and Electron Optics, 2013, 124(17), 2754-2757).

Among furoic acid derivatives, mention may be made, in particular, of 2,5-furanedicarboxylic acid (also known by the abbreviation FDCA) which may be particularly useful in polymerization reactions in order to obtain, for example, polyesters, polyamides and polyurethanes. It may also be used in pharmacology.

Furoic acid may also be easily hydrogenated to form tetrahydrofuric acid, which is a very important intermediate in the pharmaceutical industry.

There is therefore a real interest in an economically-advantageous method for the preparation of furoic acid derivatives.

One conventional approach is to oxidize the furfural in an alkaline medium in the presence of a catalyst. It should be noted that the use of an alkaline medium is necessary to achieve good catalytic performance in the oxidation reaction.

As an illustration of this approach may be mentioned, in particular, the alkali oxidation of furfural with the aid of metal catalysts in the presence of gaseous oxygen ($O_2$) (Tian et al., Molecules, 2008, 13(4), 948-957; Harrisson et al., Org Synth., 1956, 36, 36, and the document JP26001111B4 of Terai et al., or with the help of chromate salts (Hurd et al., 1. Am. Chem. Soc., 1933. 55(3), 1082-1084, and Chakraborty et al., Synthetic Communications, 1980, 10(12), 951-956), or in the presence of hydrogen peroxide ($H_2O_2$) (Corma et al. Chem. Rev., 2007, 107(6), 2411-2502) or alternatively carbon-supported Pt—Pb bimetallic catalysts (Corma et al., Chem Rev., 2007, 107(6), 2411-2502); Verdeguer et al., J. Chem. Biotechnol., 1994, 61, 97-102, and Verdeguer et al., J. Chem. Biotechnol., 1994, 112, 1-11).

Although these methods lead, for the most part, to high yields of furoic acid salts, they are unfortunately not totally satisfactory.

Thus, they have the major drawback of requiring at least one separation and conversion step subsequent to the oxidation step in order to obtain furoic acid free of its alkaline salt. This approach therefore leads to the production of large quantities of salts that are generally of little or no value.

It has also been shown that the metal catalysts used are easily poisoned during this step, making them inactive. In addition, the leaching of metal particles responsible for a gradual deactivation of the catalysts is also very often noted.

It has therefore been noted that the need to carry out the reaction in an alkaline medium has the undesirable side effect of deactivating the catalyst, in particular because of the degradation of the catalyst support.

Thus, in industrial practice, furoic acid is synthesized using $AgO/Cu_2O$ catalysts. However, such a method suffers from the need for a high catalyst load, the use of a diluted medium, and the existence of side reactions. Furfural undergoes not only oxidation to furoic acid, but also secondary reactions resulting from cleavage of the furoic cycle. In addition, the catalyst must be periodically regenerated insofar as the $Cu_2O$ phase is not stable.

Another approach to the chemical synthesis of furoic acid imposes a preliminary Canizzaro reaction from furfural in an aqueous NaOH solution to obtain furfuryl alcohol and sodium 2-furanecarboxylate. The next step is the reaction of sodium 2-furanecarboxylate with sulfuric acid to obtain furoic acid. The major disadvantage of this method is the limitation of the theoretical yield of furoic acid to 50% and the large-scale generation of sodium hydrogen sulphate which must be removed from the reaction mixture.

Furoic acid may also be synthesized via biotechnological methods (Perez et al., African Journal of Biotechnology, 2009, 8(10), 2279-2282, Eilers et al., Planta, 1970, 94, 253-264; Luna et al., Rev. Mex. Ciencias Farmacéuticas, 1997, 28, 17-19, and the documents CU22371A1 and WO9308293A1) using the action of certain microorganisms or fungi among which one may cite mushrooms such as those of the species *Neurospora crassa* and *Neurospora ascospora*, yeasts such as *Saccharomyces cerevisiae*, and bacteria such as those of the genus *Acetobacter, Bacillus, Zooglea, Nocardia* and *Pseudomonas*.

Thus, by way of example, furoic acid may be prepared by oxidation of furfural using a biocatalytic microbial preparation with *Nocardia coraHina* B-276 (Perez et al., African Journal of Biotechnology, 2009, 8(10), 2279-2282). Experiments involving this microbial conversion resulted in high yields, i.e. 88% from furfural. The oxidation with *Nocardia* corallina was considered to be interesting insofar as the use of most other microorganisms leads to the production of two oxidation products, namely the corresponding acid and alcohol. In addition, no destruction of the furan cycle was observed. However, as explained below, drawbacks remain.

The methods currently considered for preparing furoic acid from furfural therefore do not give complete satisfaction. In the case of biotechnological methods, the main drawbacks are the complexity of implementation of the method, the separation of the final products from the mixture of reagents and also the need to use substrates of high purity and a very diluted medium. In addition, in the case of the aforementioned *Nocardia* coraHina B-276 cells, the yield of furoic acid is only 88% and is obtained after 8 hours of reaction.

The most important drawbacks of the existing chemical methods are related, in particular, to the need to work in an alkaline medium. As mentioned above, this constraint has the undesirable effect, on the one hand, of requiring a subsequent treatment of secondary and/or intermediate products while, on the other hand, of affecting the stability of some of the catalysts.

There is, therefore, a particular interest for a heterogeneous catalysis method without the aforementioned drawbacks.

Thus, one of the objectives of the invention is to propose a method in heterogeneous catalysis, making it possible to directly produce furoic acid or one of its free derivatives in water (and not in the form of alkaline salt) with a very high yield.

Another objective of the invention is to provide a heterogeneous catalysis method that does not require working in an alkaline medium, and thus makes it possible to overcome the phenomenon of degradation of the catalyst support and the loss of metal residues generally encountered under alkaline conditions.

Another object of the present invention is to provide a heterogeneous catalysis method for obtaining high yields of furoic acid and advantageously in a reduced reaction time.

Another object of the present invention is to provide a method using a heterogeneous catalyst that may be easily recycled without requiring prior treatment.

Thus, the present invention relates to a method for preparing furoic acid or a derivative thereof of formula (I):

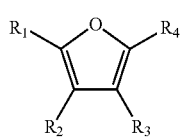
(I)

in which $R_1$, $R_2$, $R_3$ and $R_4$ represent, independently of each other, a hydrogen atom, a linear or branched $C_1$-$C_6$ alkyl group, a —C(=O)—H group or a —COOH group, provided that at least one of $R_1$, $R_2$, $R_3$ and $R_4$ groups is a COOH group, by heterogeneous catalytic oxidation of furfural or one of its derivatives of formula (II):

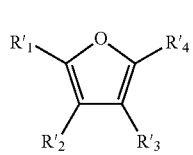
(II)

in which $R'_1$, $R'_2$, $R'_3$ and $R'_4$ represent, independently of one another, a hydrogen atom, a linear or branched $C_1$-$C_6$ alkyl group or a —C(=O)—H group, provided that at least one of $R'_1$, $R'_2$, $R'_3$ and $R'_4$ groups is a —C(=O)—H group, characterized in that the oxidation is carried out in the presence of a supported catalyst based on gold nanoparticles and in a non-alkaline aqueous medium.

For the purposes of the present invention, the term "oxidation" means the conversion of at least one aldehyde —C(=O)—H function included in formula (II) into at least one carboxylic —COOH function included in formula (I).

In the context of the present invention, a non-alkaline aqueous medium (or non-basic aqueous medium) denotes a non-alkaline pH medium, i.e. a pH of less than 8 and preferably not more than 6.

According to a preferred embodiment, this aqueous medium is devoid of organic solvent.

According to a particularly preferred embodiment, this aqueous medium consists of water as a solvent medium.

In the context of the present invention, a $C_1$-$C_6$ alkyl group denotes an alkyl group comprising from 1 to 6 carbon atoms. Such an alkyl group may be linear or branched and may be selected from methyl, ethyl, propyl, isopropyl, butyl, isobutyl, tert-butyl, pentyl, hexyl.

According to a particular embodiment, the method according to the invention makes it possible to obtain a furoic acid derivative of formula (I) in which at least two of the $R_1$, $R_2$, $R_3$ and $R_4$ groups represent a —COOH group.

Thus, according to this embodiment, the method according to the invention may lead to the production of a furoic acid derivative of formula (I) in which $R_1$ and $R_2$, or $R_1$ and $R_3$, or $R_1$ and $R_4$, or $R_2$ and $R_3$ each represent a —COOH group, while the other two remaining groups represent, independently of one another, a hydrogen atom or a linear or branched $C_1$-$C_6$ alkyl group, preferably a hydrogen atom.

According to a preferred embodiment, the method according to the invention makes it possible to obtain a furoic acid derivative of formula (I) in which $R_1$ and $R_4$ each represent a —COOH group, and $R_2$ and $R_3$ represent a hydrogen atom. It is then 2,5-furan dicarboxylic acid.

According to another embodiment, the method according to the invention makes it possible to obtain a furoic acid derivative of formula (I) in which $R_1$ represents a —C(=O)—H group or a —COOH group; $R_2$ and $R_3$ represent, independently of one another, a hydrogen atom or a linear or branched $C_1$-$C_6$ alkyl group; and $R_4$ is a —COOH group.

According to another particular embodiment, the method according to the invention makes it possible to obtain a furoic acid derivative of formula (I) in which only one of the $R_1$, $R_2$, $R_3$ and $R_4$ groups is a —COOH group, while the other three remaining groups are, independently of each other, a hydrogen atom or a linear or branched $C_1$-$C_6$ alkyl group.

According to another preferred embodiment, the method according to the invention makes it possible to obtain a furoic acid derivative of formula (I) in which $R_4$ is a —COOH group, and $R_1$, $R_2$, and $R_3$ represent an atom of hydrogen. It is then furoic acid itself.

Admittedly, oxidation methods of furfural using catalysts based on gold nanoparticles supported on zirconium dioxide ($ZrO_2$) or cerium dioxide ($CeO_2$) in the presence of methanol are well known, but these reactions, although carried out in the absence of a base (non-alkaline medium), lead to methyl furoate and not directly to furoic acid (Signoretto et al., Catalysts, 2013, 3, 656-670, Manzoli et al., Journal of Catalysis, 2015, Vol 330, 465-473 and Pinna et al., Catalysis Today, 2013, Volume 203, 196-201).

As is apparent from the experimental part which follows, the method according to the invention is particularly advantageous in several ways.

More specifically, it provides access to a very high yield of furoic acid or one of its derivatives, namely a yield of the order of 98%.

The conversion of a furfural derivative of formula (II) into its oxidation derivative of formula (I), in this case furoic acid for furfural, is carried out in a single step in the presence of gaseous oxygen in presence of a supported catalyst based on gold.

The method according to the invention makes use of catalytic formulations that are very effective and reactive in a non-basic medium.

This advantage allows direct access to the acid form of the compound of formula (II) and not to its alkaline salt. The subsequent step of converting this salt into acid is no longer required and the production of a large amount of salts that are of little or no value may be avoided.

In addition, the inventors have discovered that no leaching phenomenon occurs during catalytic tests with this type of catalyst In fact, the gold contents in the solutions after 4 hours and 15.5 hours of reaction were measured by ICP-OES (measurements by induced plasma analysis—optical emission spectrometry). They were found to be below the detection limit of the analyzer indicating that the passage of gold from the solid catalyst to the solution (a phenomenon known as leaching) does not occur for catalysts that are suitable for the present invention.

According to an alternative embodiment, the method of the invention comprises at least the steps of:
   (a) having a non-alkaline aqueous solution containing at least one furfural derivative of formula (II);
   (b) contacting the derivative of formula (II) of the medium (a) with gaseous oxygen in the presence of at least a catalytically-effective amount of supported gold nanoparticles and under non-alkaline conditions that are conducive to the oxidation of the furfural derivative of formula (II) to the furoic acid derivative of formula (I).

Preferably, step (b) is carried out with stirring and under a pressure of the order of 15 bars ($15 \cdot 10^5$ Pa) by heating the assembly to a temperature between 70° C. and 150° C., preferably between 90° C. to 120° C., more preferably 110° C.

The time (or duration) of reaction is adjusted to obtain a yield of furoic acid derivative of formula (I) equal to at least 80%.

This reaction time may advantageously be only 1 to 4 hours.

According to a particular embodiment, the catalyst used is gold supported on zirconium dioxide.

According to another particular embodiment, the catalyst used is gold supported on hydrotalcite.

Advantageously, as illustrated in the experimental part below, the method according to the invention makes it possible to obtain a furoic acid derivative of formula (I) and more particularly furoic acid with a high conversion, yield, selectivity and carbon balance.

For the purpose of the present invention, the terms "conversion rate" or "conversion" denote the ratio of the number of moles of furfural derivative of formula (II) reacted, divided by the number of moles of the furfural derivative of formula (II) initially introduced.

By "selectivity" is meant the ratio of the number of moles of furoic acid derivative of formula (I) obtained at the end of the reaction divided by the number of moles of the furfural derivative of formula (II) reacted.

By "yield" is meant the ratio of the number of moles of furoic acid derivative of formula (I) obtained at the end of the reaction divided by the number of moles of the furfural derivative of formula (II) initially introduced.

By "carbon balance" is meant the ratio of the number of carbon atoms present in the reactor at the end of the reaction divided by the number of carbon atoms initially present in the reactor.

Another advantage of the present invention is that the operating conditions are simple to implement and allow the direct production of the furoic acid derivative of formula (I) free of any salt, because of the absence of base in the reaction medium.

The absence of base in the reaction medium also makes it possible to avoid the degradation of the catalyst support and the leaching of metal particles in the liquid phase, which renders the catalyst recyclable for several successive uses in a closed or stable reactor under flow in open reactor.

The present invention also provides a composition comprising at least furfural and supported gold nanoparticles.

According to an alternative embodiment, this composition also contains a furfural derivative of formula (II) and, if appropriate, water.

Advantageously, the composition is non-alkaline.

Method According to the Invention

Definition of Gold Nanoparticles

The gold nanoparticles that are suitable for the invention are well known and are already commonly used in chemistry as catalysts for reactions of the hydrogenation or oxidation type as well as, in particular, in optics, electronics, pharmacology, diagnostics or therapy.

For most of these applications, the nanoparticles are attached to a solid support.

Various methods are known for the preparation of gold nanoparticles, in particular in a confined mineral medium or in a confined organic medium.

The preparation of gold nanoparticles in a confined inorganic medium may be carried out in inorganic suspensions (titanium, silica, clay), by reduction of a gold precursor in the presence of a catalyst such as that described by K. Nakamura et al. (J. Chem. Eng. Jap., 2001, 34, 1538-1544). The preparation of gold nanoparticles in a silica matrix bearing hydroxyl groups by spontaneous reduction of a gold precursor is described by P. Mukherjee et al. (Chem. Mater., 2002, 14, 1678-1684), and by T. Yokohama et al. (Journal of Colloid and Interface Science, 2001, 233, 112-116).

The gold nanoparticles that are suitable for the invention have a size of between 3 nm and 15 nm, preferably between 5 nm and 10 nm.

As stated above, the gold particles are supported.

By way of illustration of the supports which are suitable for the invention, mention may be made, in particular, of zirconium dioxide ($ZrO_2$) and hydrotalcite.

Thus, according to one embodiment, a catalyst that is suitable for the invention is gold supported on zirconium dioxide or on hydrotalcite.

According to a particular embodiment, the catalyst used is gold supported on zirconium dioxide.

The percentage by weight of gold in the Au/ZrO$_2$ catalyst for the oxidation of furfural is between 1% and 7% by weight, and is preferably equal to 3% by weight, wherein zirconium dioxide is used as the support with a low specific surface of less than or equal to 10 m$^2$/g.

As demonstrated in the experimental part below, this percentage of 3% by weight makes it possible to obtain optimum selectivity.

A relatively low percentage by weight of gold makes it possible to disperse the gold on the ZrO$_2$ surface and to increase the amount of active sites. For higher percentages, the formation of gold aggregates on the surface is possible, which may result in the formation of a less active catalyst.

When the catalyst used is Au/ZrO$_2$, the molar ratio of furfural/Au for the oxidation of furfural is between 6 and 34, and preferably this molar ratio is 6.

According to another particular embodiment, the catalyst used is gold supported on hydrotalcite.

The percentage by weight of gold in the Au/hydrotalcite catalyst for the oxidation of furfural is between 1% and 3% by weight, and is preferably equal to 2% by weight, wherein hydrotalcite is used as the support, with a low specific surface of less than or equal to 10 m$^2$/g.

As explained in the examples below, this percentage of 2% by weight makes it possible to obtain not only a high yield but also high selectivity in furoic acid.

When the catalyst used is Au/hydrotalcite, the furfural/Au molar ratio for the oxidation of furfural is between 22 and 50, preferably this molar ratio is 22.

The supported catalyst according to the invention may be prepared by any conventional method.

For example, a supported catalyst according to the invention may be prepared by dissolving a required amount (24.8 mg) of chloroauric acid hydrate (also called tetrachloroauric acid hydrate), in particular that sold under the name HAuO$_4$ by the company Alpha Aesar in a suitable amount of water (20 ml). Other gold salts may also be used for this type of preparation, such as nitrates, especially Au(NO$_3$)$_3$ or chlorides such as in particular AuCl$_3$ or Au$_2$Cl$_6$.

Then a suitable amount (1 g) of support such as zirconium dioxide or hydrotalcite is added to this solution and the mixture is stirred at a temperature between 25° C. and 50° C., preferably at room temperature (25° C.) for a period of at least 10 minutes.

Then, an amount (2 ml) of hydrazine (N$_2$H$_4$), for example that marketed in 78-82% aqueous solution by Sigma Aldrich (hydrazine hydrate) is injected into the solution. The reduction of gold is then effected spontaneously.

The solution is subsequently subjected to stirring for a period of between 30 and 60 minutes, preferably for 40 minutes at a temperature of between 25° C. and 50° C., preferably at room temperature (25° C.) until it obtains a precipitate which is filtered and then washed appropriately.

The catalyst is obtained in solid form and then dried in an oven at a temperature between 60° C. and 100° C., preferably at 80° C., for a period of between 6 and 14 hours, preferably overnight.

An example of preparation of a catalyst that is suitable for the invention is more particularly described in Example 1 below.

Reaction Conditions

The oxidation may be carried out in any manner known to those skilled in the art, in particular under oxygen or air pressure, preferably under oxygen pressure.

Preferably, the oxygen or air pressure used is such that the molar ratio O2/furfural derivative of formula (II) is greater than 2.

The pressure may especially be 10 to 20 bar (10·10$^5$ to 20·10$^5$ Pa) of air, preferably 15 bar (15·10$^5$ Pa) of air.

The oxygen partial pressure may be from 5 to 20 bars (i.e. 5·10$^5$ to 20·10$^5$ Pa), preferably from 10 to 15 bars (10·10$^5$ to 15·10$^5$ Pa), more particularly 15 bars (15·10$^5$ Pa).

Typically, the reaction temperature for the oxidation of the furfural derivative of formula (II), in particular furfural, is between 70° C. and 150° C., in particular between 90° C. and 120° C., and preferably 110° C.

However, a temperature above 120° C. is not indicated insofar as it is likely to cause the degradation of the furfural and/or the product, the formation of various carbon compounds, and a decrease in the carbon balance of the reaction. However, the deposition of carbon on the metal catalysts may cause deactivation of the catalyst.

The duration of the reaction for the oxidation of the furfural derivative of formula (II), in particular furfural, is between 1 hour and 15.5 hours, preferably between 2 hours and 4 hours. As detailed in the experimental section below, it was observed that a reaction time longer than 4 hours does not significantly increase the yield of this reaction and after a period of 15.5 hours, the furfural becomes unstable and the quantity of secondary products is no longer negligible.

The method may be implemented in continuous mode or in batch mode.

In an advantageous embodiment mode, the method according to the invention is implemented in batch mode.

In general, the method according to the invention may be applied industrially to the oxidation of furfural and its derivatives to obtain the corresponding carboxylic acid free of any salt.

The expressions "comprised between . . . and . . . " and "from . . . to . . . " are to be understood as inclusive terms, unless otherwise specified.

The examples which follow will make it possible to better understand the invention, without, however, being limiting in nature.

EXAMPLES

Example 1: Preparation of Catalysts Suitable for the Invention a) Catalyst 3% Au/ZrO$_2$ 66.5 mg of chloroauric acid hydrate (Au 49% min., from the company Alpha Aesar, 99.9%) are dissolved in 20 ml of water. 997 mg of zirconium dioxide, monoclinic with a baddeleyite structure from Sigma Aldrich, are added to this solution. The mixture is then stirred at room temperature (25° C.) for 10 minutes.

2 ml of hydrazine (N$_2$H$_4$, 80% aqueous solution, from Sigma Aldrich) are then injected into the solution. The reduction of gold then takes place spontaneously.

The solution is stirred for 40 minutes at room temperature (25° C.) until a purple precipitate is obtained. The precipitate thus obtained is then filtered under vacuum and washed 3 times with water (3 times 20 ml) and once with acetone (20 ml).

The solid thus obtained is subsequently dried overnight in an oven at 80° C.

b) Catalyst 2% Au/hydrotalcite 44.4 mg of chloroauric acid hydrate (Au 49% min., from the company Alpha Aesar, 99.9%) are dissolved in 20 ml of water. 912 mg of hydrotalcite synthesized in the laboratory with a low specific surface area of 10 m$^2$/g are added to this solution. The mixture is then stirred at room temperature (25° C.) for 10 minutes.

2 ml of hydrazine (N$_2$H$_4$, 80% aqueous solution, from Sigma Aldrich) are then added to the solution. The reduction of gold then takes place spontaneously.

The solution is stirred for 40 minutes at room temperature (25° C.) until a purple precipitate is obtained. The precipitate thus obtained is then filtered under vacuum and washed 3 times with water (3 times 20 ml) and once with acetone (20 ml).

The solid thus obtained is subsequently dried overnight in an oven at 80° C.

Example 2: General Procedure for the Oxidation of a Furfural Derivative of Formula (II) and More Particularly of Furfural The procedure detailed below is the general procedure used for the catalytic tests whose results are set forth in Example 3 of the present invention.

The catalytic tests are carried out in a 50 ml autoclave reactor equipped with a thermocouple (Top Industrie Autoclave 2456). The procedure for a standard test is detailed below.

The amount is adjusted according to the test to be performed, for example 50 mg (from 10 to 150 mg) of furfural are added to distilled water (10 ml) and stirred magnetically for 10 minutes. 9 ml of the furfural solution are then added to the autoclave reactor under atmospheric pressure and at room temperature (25° C.).

100 mg of catalyst (variable nature according to the test carried out) are then added to the reaction mixture at ambient temperature (25° C.). The catalysts suitable for the invention to be tested, namely Au/ZrO$_2$ and Au/hydrotalcite are those prepared according to the protocol of Example 1.

10 ml of distilled water are again added to the reactor at ambient temperature (25° C.). The reactor is then closed and the magnetic stirring is set at 900 rpm at room temperature (25° C.). Then, the reactor is purged three times with oxygen. The 02 pressure is then set at 15·10$^5$ Pa (15 bar) and the reactor is closed. The temperature is then set to the desired value according to the test to be performed, namely 90° C., 110° C. and 120° C., as indicated in the examples below.

The reaction time imposed for these tests may also be variable depending on the parameter tested, as specified below; it may be 1 hour, 2 hours, 4 hours or 15.5 hours.

Then, the reactor is cooled to room temperature (25° C.) and the resulting solution is taken from the reactor, centrifuged to separate it from residual solid catalyst particles and analyzed by HPLC (high performance liquid chromatography) whose protocol is detailed below.

HPLC Analysis

The reaction mixture is filtered using an HPLC filter (2.5 μm), and then diluted 5 times with water. The analysis by liquid chromatography is carried out on a Shimadzu UFLC-MS 20-20 HPLC chain equipped with a Phenomenex Synergi 2.5 μm Hydro-RP 100 A column. The column is purged at 0.5 ml/min at room temperature. (25° C.) with a 0.1% trifluoroacetic acid aqueous solution as the mobile phase, for 12 minutes. The retention times for each compound are verified using commercial standards. The conversion, yields and selectivity are determined by the calibration curve method (performed for each compound).

The conversions are calculated as follows:

$$\frac{\text{Furfural}_{Tinitial} - \text{Furfural}_{Tfinal}}{\text{Furfural}_{Tinitial}} \times 100$$

While the yield is calculated as follows:

$$\frac{\text{Product}_{Tfinal}}{\text{Furfural}_{Tinitial}} \times 100$$

The reaction rate is calculated as follows:

$$\frac{\text{Furfural}_{Tinitial} - \text{Furfural}_{Tfinal}(\text{mmol})}{\text{time}(\text{min}) \cdot \text{weightAu}(\text{mg})}$$

Example 3: Catalytic Performance Observed with a Supported Catalyst Based on Gold 3.1 Influence of Temperature The oxidation method as described above is carried out with the Au/ZrO$_2$ catalyst according to the invention as synthesized as an example 1a). The percentage by weight of gold in this catalyst is 3% by weight.

The O$_2$ pressure, the stirring speed and the amount of catalyst imposed are those indicated in Example 2. The amount of furfural used is 50 mg, and the reaction time is 1 hour.

The reaction temperatures tested are 90° C., 110° C. and 120° C.

For each of these reaction temperatures, the conversion rate of furfural, furoic acid yield, furoic acid selectivity and carbon balance are summarized in Table 1 below.

TABLE 1

| Temperature ° C. | Furfural conversion rate (%) | Yield in furoic acid (%) | Selectivity in furoic acid (%) | Carbon balance (%) |
|---|---|---|---|---|
| 90 | 10.7 | 6.1 | 57.5 | 95.5 |
| 110 | 35.0 | 29.7 | 84.7 | 95.0 |
| 120 | 46.0 | 36.5 | 79.2 | 90.4 |

It appears that the best selectivity is observed with a reaction temperature of 110° C.

3.2 Influence of Au Concentration

A preliminary test, excluding the invention, is carried out in the presence of ZrO$_2$ alone, i.e. without gold nanoparticles. It should be noted that the oxidation reaction of furfural does not occur.

Then, the oxidation method as described above is carried out with the Au/ZrO$_2$ catalyst according to the invention. Four different percentages by weight of gold were tested for this catalyst, namely 1%, 3%, % 5% and 7% by weight. The catalysts are prepared according to the synthesis protocol described in Example 1a), optionally adapted according to the desired weight percentage.

The required O$_2$ pressure, stirring rate and catalyst amount are as indicated in Example 2. The amount of furfural used is 50 mg, the reaction temperature is 110° C., and the reaction time is 4 hours.

For each of the percentages by weight of gold, the molar ratio of furfural/Au, the conversion rate of furfural, the yield in furoic acid, the selectivity of furoic acid and the carbon balance are summarized in Table 2 below.

TABLE 2

| Catalyst | Furfural/ Au molar ratio | Furfural conversion rate (%) | Yield in furoic acid (%) | Selectivity in furoic acid (%) | Carbon balance (%) |
|---|---|---|---|---|---|
| 1% Au/ZrO$_2$ | 100 | 7.0 | 3.9 | 55.5 | 96.9 |
| 3% Au/ZrO$_2$ | 30 | 35.0 | 29.7 | 84.7 | 95.0 |
| 5% Au/ZrO$_2$ | 20 | 45.1 | 35.4 | 78.5 | 90.3 |
| 7% Au/ZrO$_2$ | 14 | 38.8 | 32.1 | 82.7 | 93.3 |

It appears that when the gold load increases, the conversion to furfural also increases, but, at the same time, the impact on the selectivity is rather limited, at least for loads greater than 3% by weight.

The best selectivity is observed with Au/ZrO$_2$ 3% by weight.

3.3 Influence of the Reaction Time

The oxidation method as described above is carried out with the Au/ZrO$_2$ catalyst according to the invention as synthesized as in example 1a). The percentage by weight of gold in this catalyst is 3% by weight.

The O$_2$ pressure, the stirring rate and the amount of catalyst imposed are those indicated in Example 2. The amount of furfural used is 50 mg, and the reaction temperature is 110° C.

The reaction times tested are 1 hour, 2 hours, 4 hours and 15.5 hours.

For each of these times, the conversion rate of furfural, yield and selectivity (named Select) in furoic acid, secondary products such as 2(5H)-furanone, maleic acid, and carbon dioxide as well as the carbon balance are summarized in Table 3 below.

TABLE 3

| | Duration (h) | | | | | | | |
|---|---|---|---|---|---|---|---|---|
| | 1 | | 2 | | 4 | | 15.5 | |
| | Conversion (%) | | Conversion (%) | | Conversion (%) | | Conversion (%) | |
| Furfural conversion rate (%) | 35.0 | | 51.7 | | 68.0 | | 91.9 | |
| | Yield (%) | Select (%) | Yield (%) | Select (%) | Yield (%) | Select (%) | Yield (%) | Select (%) |
| Furoic acid | 29.7 | 84.7 | 45.0 | 87.0 | 54.1 | 79.6 | 50.0 | 54.5 |
| 2(5H)furanone | 0.2 | 0.4 | 0.9 | 1.7 | 1.4 | 2.1 | 8.5 | 9.2 |
| Maleic acid | 0.1 | 0.5 | 0.4 | 0.7 | 0.4 | 0.6 | 2.5 | 2.7 |
| Carbondioxide | 0.0 | 0.0 | 0.2 | 0.3 | 0.2 | 0.3 | 1.4 | 1.5 |
| Carbon balance (%) | 95.0 | | 94.6 | | 87.9 | | 69.1 | |

Too long reaction times have revealed the instability of furfural. After 2 hours, the carbon balance and the selectivity in furoic acid decrease. After a period of 15.5 hours, these decreases are even greater and the amount of secondary products simultaneously increases.

3.4 Influence of the Nature of the Support

The oxidation method as described above is carried out with different catalysts based on gold nanoparticles, namely Au/CeO$_2$, Au/MgO, Au/hydrotalcite as synthesized as Example 1 b) and Au/ZrO$_2$. as synthesized as an example 1a). The Au/CeO$_2$ and Au/MgO catalysts according to the invention may be prepared by any method known to those skilled in the art and in particular according to those described in example 1 above. The percentage by weight of gold in these catalysts is 2% or 3% by weight, as specified in Table 4 below.

The required O$_2$ pressure, stirring rate and catalyst amount are as shown in Example 2. The reaction temperature is 110° C. and the reaction time is 2 hours.

As for the amount of furfural used, it is 50 mg.

For each of these catalysts, the conversion rate of furfural, the yield and selectivity in furoic acid, and the carbon balance are summarized in Table 4 below.

TABLE 4

| Support | Furfural conversion rate (%) | Yield in furoic acid (%) | Selectivity in furoic acid (%) | Carbon balance |
|---|---|---|---|---|
| 3% Au/CeO$_2$ according to the invention | 56.6 | 38.4 | 67.8 | 84.3 |
| 3% Au/MgO according to the invention | 33.1 | 8.8 | 26.5 | 75.7 |
| 2% Au/hydrotalcite according to the invention | 78.5 | 71.8 | 91.4 | 93.3 |
| 3% Au/ZrO$_2$ according to the invention | 51.7 | 45.0 | 87.0 | 94.6 |

It appears that low activity is observed in the case of Au supported on $CeO_2$ or MgO.

A comparison between the catalytic tests carried out with different supports shows that, by using a supported catalyst of the hydrotalcite type, much better performances are obtained (higher conversion and selectivity).

3.5 Influence of the Molar Ratio Furfural/Au 3.5.1 Catalyst $Au/ZrO_2$ According to the Invention The oxidation method as described above is carried out with the $Au/ZrO_2$ catalyst according to the invention as synthesized as an Example 1a). The percentage by weight of gold in this catalyst is 3% by weight.

The $O_2$ pressure, the stirring speed and the amount of catalyst imposed are those indicated in Example 2. The reaction temperature is 110° C. and the reaction time is 4 hours.

As for the amount of furfural used, it is adjusted to obtain three furfural/Au molar ratios of 34, 18 and 6 respectively.

For each of these ratios, the conversion rate of furfural, yield and selectivity in furoic acid, and the carbon balance are summarized in Table 5 below.

TABLE 5

| Furfural/Au molar ratio | Furfural conversion rate (%) | Yield in furoic acid (%) | Selectivity in furoic acid (%) | Carbon balance |
|---|---|---|---|---|
| 34 | 68.0 | 54.1 | 79.6 | 87.3 |
| 18 | 78.4 | 66.1 | 84.2 | 89.5 |
| 6 | 87.8 | 76.6 | 87.3 | 90.0 |

From these results, it appears that the Furfural/Au molar ratio has a strong influence on performance.

In fact, the lower the molar ratio, the higher the conversion, the selectivity and, therefore, the yield in furoic acid are high.

3.5.2 Au/Hydrotalcite Catalyst According to the Invention

The oxidation method as described above is carried out with the Au/hydrotalcite catalyst according to the invention as synthesized in Example 1b). The percentage by weight of gold in this catalyst is 2% by weight.

The $O_2$ pressure, the stirring speed and the amount of catalyst imposed are those indicated in Example 2. The reaction temperature is 110° C. and the reaction time is 2 hours.

As for the amount of furfural used, it is adjusted to obtain a furfural/Au molar ratio of 22.

The conversion rate of furfural, yield and selectivity in furoic acid, and the carbon balance are summarized in Table 6 below.

TABLE 6

| Furfural/Au molar ratio | 22 | |
|---|---|---|
| Conversion (%) | | |
| Furfural | 98.2 | |
| | Yield (%) | Selectivity (%) |
| Furoic acid | 96.7 | 98.5 |
| Carbon balance | | 98.5 |

Thus, the use of a 2% by weight Au/hydrotalcite catalyst makes it possible to obtain a high yield of furoic acid with a high selectivity.

Example 4: Plasma Analyses Induced Possible Losses of Metal Residues

Induced plasma analyses (ICP) of the reaction solution for the tests (catalytic tests carried out with the 3% $Au/ZrO_2$ catalyst according to the invention as synthesized in Example 1a) after 1 and 15.5 hours confirmed that no loss of metal residues occurred during the reaction.

ICP optical emission spectrometry measurements (ICP-OES) are performed on an Agilent 720-ES spectrometer. The samples are prepared by digestion using aqua regia. The amount of gold in the solution is determined using the calibration curves obtained with the standard commercial solutions.

Table 7 below summarizes the data collected, including the mean intensity and RSD intensity (Relative Standard Deviation, coefficient of variation) after 1 hour (white) and 15.5 hours of reaction (catalytic test).

TABLE 7

| | Au 211,068 |
|---|---|
| White = reference (after 1 hour of reaction) | |
| Average intensity | 14,286 |
| Intensity % RSD | 26,781 |
| Measured after 15.5 hours of reaction | |
| Average intensity | 12,123 |
| intensity % RSD | 50.195 |
| Intensity/white intensity ratio | 0.85 |

What is claimed is:

1. A method for the preparation of furoic acid, comprising heterogeneous catalytic oxidation of furfural,
wherein the oxidation is carried out in a single step in the presence of a supported catalyst based on gold nanoparticles and in a non-alkaline aqueous medium.

2. The method according to claim 1, wherein the non-alkaline aqueous medium is a non-alkaline pH medium having a pH of less than 8.

3. The method according to claim 1, wherein the aqueous medium is devoid of organic solvent.

4. The method according to claim 1, wherein the aqueous medium consists of water as a solvent medium.

5. The method according to claim 1, the method comprising:
(a) providing a non-alkaline aqueous solution containing at least furfural;
(b) contacting furfural of the medium (a) with gaseous oxygen in the presence of at least a catalytically-effective amount of supported gold nanoparticles and under non-alkaline conditions conducive to the oxidation of furfural to furoic acid.

6. The method according to claim 1, wherein the oxidation is carried out under a partial pressure of oxygen of between $5 \cdot 10^5$ Pa and $20 \cdot 10^5$ Pa.

7. The method according to claim 1, wherein the oxidation is carried out at a temperature between 70° C. and 150° C.

8. The method according to claim 1, wherein the catalyst is gold supported on zirconium dioxide or on hydrotalcite.

9. The method according to claim 1, wherein the catalyst is gold supported on hydrotalcite.

10. A method for the preparation of furoic acid or of one of its derivatives of formula (I):

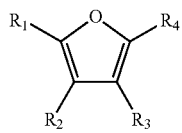 (I)

in which $R_1$, $R_2$, $R_3$ and $R_4$ represent, independently of each other, a hydrogen atom, a linear or branched $C_1$-$C_6$ alkyl group, a —C(=O)—H group or a —COOH group,
provided that at least one of $R_1$, $R_2$, $R_3$ and $R_4$ is a —COOH group,
by heterogeneous catalytic oxidation of furfural or a derivative thereof of formula (II):

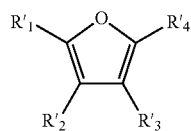 (II)

in which $R'_1$, $R'_2$, $R'_3$ and $R'_4$ represent, independently of each other, a hydrogen atom, a linear or branched $C_1$-$C_6$ alkyl group or a —C(=O)—H group,
provided that at least one of the $R'_1$, $R'_2$, $R'_3$ and $R'_4$ groups is a —C(=O)—H group, wherein the oxidation is carried out in a single step in the presence of a supported catalyst based on gold nanoparticles and in a non-alkaline aqueous medium, wherein the catalyst is gold supported on zirconium dioxide.

11. The method according to claim 10, wherein the percentage by weight of gold in the catalyst Au/ZrO$_2$ for the oxidation of furfural is between 1% and 7% by weight.

12. The method according to claim 11, wherein zirconium dioxyde, used as a support, has a specific surface of less than or equal to 10 m$^2$/g.

13. The method according to claim 10, wherein the furfural/Au molar ratio for the oxidation of furfural is between 6 and 34.

14. The method according to claim 9, wherein the percentage by weight of gold in the Au/hydrotalcite catalyst for the oxidation of furfural is between 1% and 3% by weight.

15. The method according to claim 14, wherein the hydrotalcite, used as a support, has a specific surface less than or equal to 10 m$^2$/g.

16. The method according to claim 9, wherein the furfural/Au molar ratio for the oxidation of furfural is between 22 and 50.

17. The method according to claim 1, wherein the size of the gold nanoparticles in the catalyst for the oxidation of furfural is between 3 nm and 15 nm.

18. The method according to claim 1, wherein the method is implemented in continuous mode or in batch mode.

* * * * *